Figure 1:
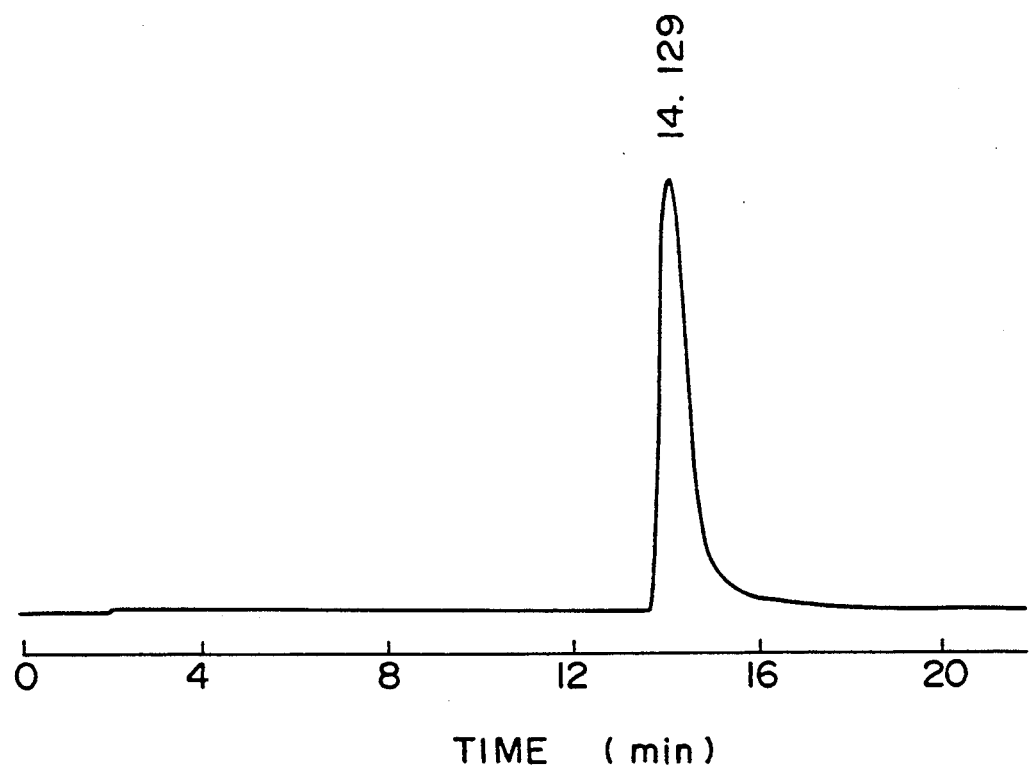

United States Patent [19]
Uchida et al.

[11] Patent Number: 5,306,617
[45] Date of Patent: Apr. 26, 1994

[54] PHENYTOIN DERIVATIVES

[75] Inventors: Takafumi Uchida, Oberwil, Switzerland; Hiroshi Ishikawa, Hino; Koichi Koyama, Machida, both of Japan; Yoshihiro Kurano, Akigawa; Yoshiaki Uchida, Hachioji, both of Japan

[73] Assignee: Fujirebio Inc., Tokyo, Japan

[21] Appl. No.: 744,411

[22] Filed: Aug. 13, 1991

[30] Foreign Application Priority Data

Aug. 16, 1990 [JP] Japan .................................. 215076

[51] Int. Cl.$^5$ .................. C12Q 1/68; C07H 5/04; C07H 17/00; C07H 19/06
[52] U.S. Cl. .................. 425/6; 536/18.7; 536/23.1; 536/24.3; 536/26.26
[58] Field of Search .................. 435/6, 7.5, 6.91; 536/27, 18.7, 23.1, 24.3, 26.26; 436/518

[56] References Cited

U.S. PATENT DOCUMENTS 4,213,964  7/1980  Buckler ........................ 530/362
4,752,568  6/1988  Danielson et al. ............. 435/188

FOREIGN PATENT DOCUMENTS 0292170  11/1988  European Pat. Off. .

OTHER PUBLICATIONS

Langer et al., (1981) Proc. Natl. Acad. Sci. U.S.A. 78(11):6633–6637.
Rigos et al., (1986) Proc. Natl. Acad. Sci. U.S.A. 83:9591–9595.

*Primary Examiner*—Robert A. Wax
*Assistant Examiner*—Migual Escallon
*Attorney, Agent, or Firm*—Sherman and Shalloway

[57] ABSTRACT

A phenytoin derivative represented by formula (I)

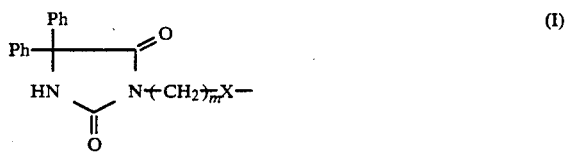

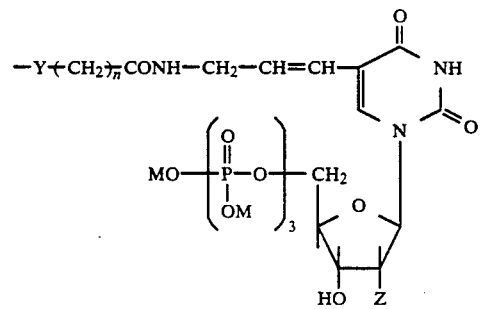

wherein
Ph denotes a phenyl group,
X denotes —O—, —NH— or —CH$_2$—,
Y denotes —CO— or —CH$_2$—,
Z denotes a hydrogen atom or a hydroxyl group,
M denotes a salt-forming cation, and
m and n are each an integer of 0 to 8 and m+n is at least 2.

Said compound is useful to produce a phenytoin-labelled DNA or RNA probe. When using such a probe, DNA or RNA in the specimen can be detected with high sensitivity.

12 Claims, 1 Drawing Sheet

PHENYTOIN DERIVATIVES

This invention relates to a phenytoin derivative, and more specifically to a phenytoin derivative represented by formula (I)

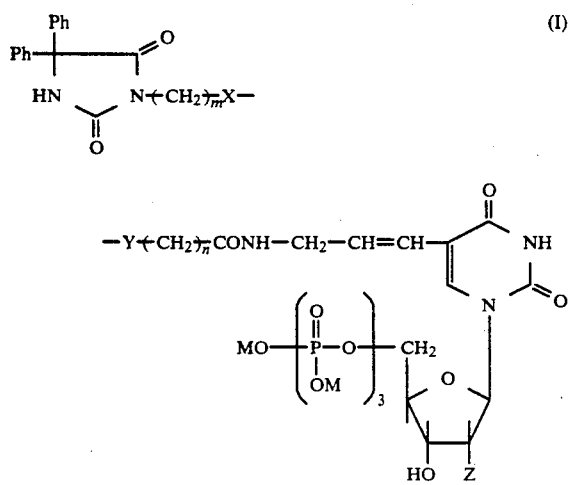

wherein
Ph denotes a phenyl group,
X denotes —O—, —NH— or —CH$_2$—,
Y denotes —CO— or —CH$_2$—,
Z denotes a hydrogen atom or a hydroxyl group,
M denotes a salt-forming cation, and
m and n are each an integer of 0 to 8 and m+n is at least 2,
a phenytoin-labelled nucleic acid (DNA or RNA) probe, and use of said compound in detecting specific nucleic acid.

Diagnosis using nucleic acid is a method for detecting genes or abnormality and pathogens that cause infection, etc., at a level of nucleic acid, and is effective as prepatent diagnosis of diseases or early diagnosis. A labelled DNA probe or a labelled RNA probe is used in this diagnosis. Radioisotopes such as $^{32}$P, $^{125}$I, etc., and non-radioisotopic substances such as biotin, digoxigenin, etc., are used to form the labelled substances.

The radioisotopes are adopted in a method for sensitively detecting a trace amount of nucleic acid, but require special treating equipment and facilities and are regulated in treating wastes. Moreover, radioisotopes, $^{32}$P and $^{125}$I are short in half-life and become unusable for a short period of time. In order to conquer these defects, a proposal has been made to use non-radioisotopic substances such as biotin, digoxigenin, etc., as labelling substances instead of radioisotopes.

To be concrete, it is known to use, as a DNA or RNA labelling substance, a biotindeoxyuridine triphosphate derivative (hereinafter abbreviated as "biotin dUTP") which is a combinatin of biotin and a deoxyuridine derivative or a biotinuridine triphosphate derivative (hereinafter abbreviated as "biotin UTP" [see P. R. Langer, et al., Proc. Nath. Acad. Sci., USA, 78, 6633 (1981); B. Rigas, et al., ibid, 83, 9591 (1986); and P. S. Nelson, et al., Nucleosides and Nucleotides, 3, 233 (1986)], or a digoxigenindeoxyuridine triphosphate derivative (hereinafter abbreviated as "digoxigenin dUTP") which is a combination of digoxygenin and a deoxyuridine derivative or a digoxigeninuridine triphosphate derivative (hereinafter abbreviated as "digoxigenin UTP") which is a combination of digoxigenin and an uridine derivative [see PCT International Laid-open WO 89/06698].

The above biotin UTP, biotin dUTP, digoxigenin UTP and digoxigenin dUTP which are reagents for introducing the non-radioisotopic substances into a DNA or RNA probe as labelling substances can stably be stored and used without the need of special facilities.

The biotin UTP or the biotin dUTP can be used in a method for detecting DNA or RNA in a specimen in which said biotin UTP or biotin dUTP is introduced into a DNA probe by an enzymatic reaction, and reacted with enzymatically labelled avidin, and then with RNA or DNA in the specimen, followed by measuring color development or luminescence given by the enzymatic reaction. Said method is used, for example, in the direct detection of virus RNA or DNA in the specimen, but suffers a problem that during the measurement, an aspecific reaction is often observed and a sufficient pretreating operation is therefore required in the actual measurement.

Further, digoxigenin UTP or digoxigenin dUTP is used together with an enzymatically labelled anti-digoxigenin antibody and can be subjected to the measurement like biotin UTP or biotin dUTP.

In the method using said digoxigenin, an aspecific reaction observed in a biotin-avidin system is not found so much, but sensitivity decreases at times. One reason is that since digoxigenin is a relatively high-molecular compound as hapten, it inhibits hybridization of the digoxigenin-labelled RNA or DNA probe and the specimen RNA or DNA, which leads to decrease in sensitivity.

The present inventors have made studies about non-radioisotopic labels that enable target DNA or RNA in a specimen to be detected without causing such an aspecific reaction, and have, consequently, found that a phenytoin derivative of formula (I) is quite suitable.

Nucleic acid containing the phenytoin derivative introduced therein, i.e., the phenytoin-labelled DNA or RNA, is used as a labelled probe in combination with an anti-phenytoin monoclonal antibody proposed before by the present inventors (see Japanese Laid-open Patent Application No. 138,992/1990), so that DNA or RNA in the specimen, such as viral hepatitis type B (HBV) DNA in a serum, can be measured with quite high sensitivity.

In formula (I), examples of the salt-forming cation denoted by M include ions of alkali metals such as lithium, potassium and sodium; ions of alkaline earth metals such as magnesium, calcium and barium; and an ammonium ion. Of these, sodium ions are preferable.

When the phenytoin derivative of formula (I) is introduced into nucleic acid and used as a labelled nucleic acid probe, it is advisable from the aspects of ease in production of the labelled probe and ease in combining the phenytoin portion of the labelled probe with the antibody that in formula (I), m is 0 to 8, especially 4 to 6, n is 0 to 8, especially 2 to 3, and m+n is 2 to 16, especially 6 to 9.

The phenytoin derivative of formula (I) provided by this invention can be produced, for example, via a route shown by the following Reaction Scheme A.

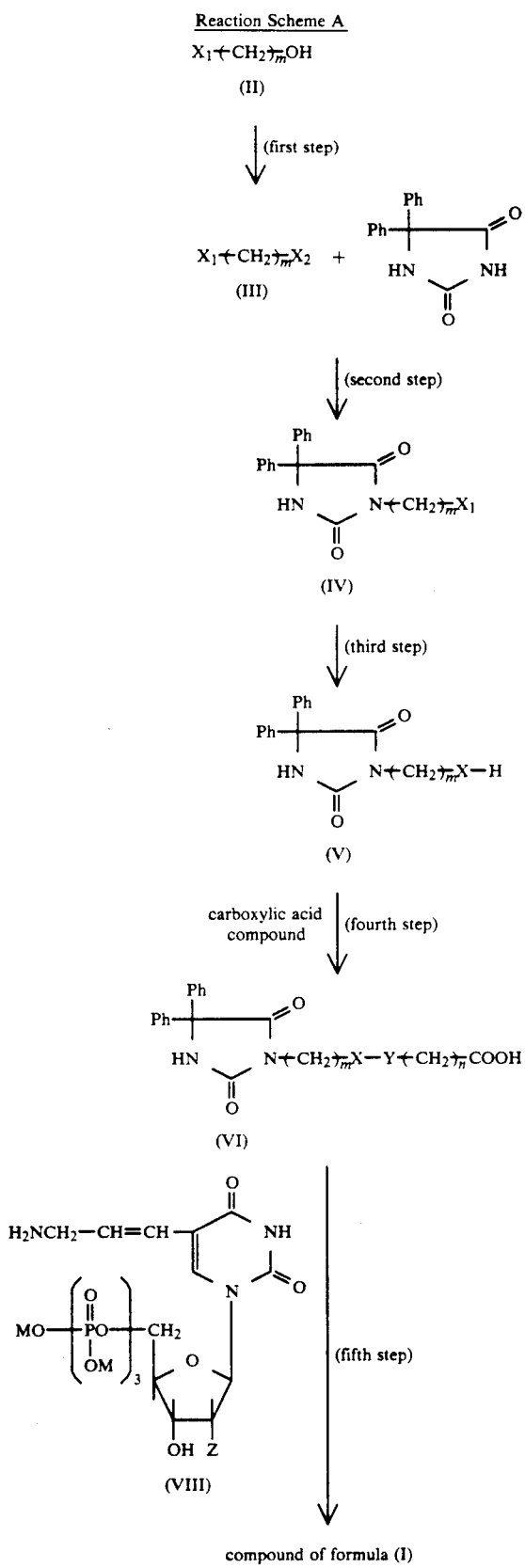

Reaction Scheme A compound of formula (I)

wherein

X₁ denotes a protected amino group or a protected hydroxyl group,

X₂ denotes a halogen atom or an organosulfonic acid residue such as a p-toluenesulfonic acid residue or a methanesulfonic acid residue, and Ph, X, Y, Z, M, m and n are as defined above.

The respective reaction steps are described more specifically.

First Step

The first step is a step of halogenating or organically sulfonating an alcohol compound of formula (II) to form a halogenated compound or a sulfonic acid ester.

The halogenation or the organic sulfonation of the alcohol of formula (II) can be carried out by reacting the alcohol of formula (II) with a halogenating agent or an organosulfonic acid derivative. Examples of the halogenating agent include thionyl halides such as thionyl chloride and thionyl bromide; and phosphorus halide derivatives such as phosphorus pentachloride, phosphorus pentabromide and phosphorus oxychloride. Examples of the organosulfonic acid derivatives include p-toluenesulfonyl chloride, p-toluenesulfonyl bromide, methanesulfonyl chloride and methanesulfonyl bromide.

The reaction can be conducted in the absence of a solvent or in an inert solvent. When using the inert solvent, examples thereof are halogenated hydrocarbons such as methylene chloride and chloroform, and aromatic hydrocarbons such as benzene and toluene.

The reaction temperature is usually about $-5$ to about $50°$ C. The alcohol compound of formula (II) which is a starting material used to practise the first step is an amino alcohol compound having a protected amino group or a diol compound having one protected hydroxyl group. Examples of the alcohol compound are alcohol compounds having a protected amino group or a protected hydroxyl group, such as ethylene glycol, propylene glycol, 1,4-butanediol, 1,5-pentanediol, 1,6-hexanediol, 1,7-heptanediol, 1,8-octanediol, aminoethanol, 3-aminopropanol, 4-aminobutanol, 5-aminopentanol, 6-aminohexanol, 7-aminoheptanol and 8-aminooctanol. The protective groups of the amino group and the hydroxyl group can be usual protective groups capable of being easily cleaved by an ordinary eliminating means such as hydrolysis or hydrogenolysis. Examples of the protective group of the amino group include a tert-butoxycarbonyl group, a benzyloxycarbonyl group, and a phthaloyl group. Examples of the protective group of the hydroxyl group include an acetyl group, a methoxyethyl group, and a tetrahydropyranyl group.

The alcohol compound of formula (II) can be formed by a condensation reaction of the amino alcohol or diol compound and the alcohol as the protective group in the inert solvent.

Second Step

The second step is a step of forming the phenytoin derivative of formula (IV) by the reaction of the compound of formula (III) obtained in the first step and phenytoin (5,5-diphenyl-2,4-imidazolidinedione).

It is advisable to conduct the reaction of this step in the presence of a base. Examples of the base are hydroxides, carbonates and hydrogencarbonates of alkali metals such as potassium carbonate, sodium carbonate, potassium hydrogencarbonate, sodium hydrogencarbonate, sodium hydroxide and potassium hydroxide. The amount of the base is not strictly limited; it is usually at least 1 equivalent, preferably 1 to 3 equivalents based on the compound of formula (III). It is also advisable to effect the reaction in a solvent. Examples of the solvent are inert solvents, e.g., amides such as dimethylformamide (DMF); ethers such as diethyl ether, tetrahydrofuran, dioxane and dimethoxyethane; and aromatic hydrocarbons such as benzene, toluene and xylene. They can be used either singly or in combination.

In general, the reaction can efficiently be carried out at a temperature of about 0° to about 50° C.

The first and second steps can be performed in series without isolating the compound of formula (III) on the way.

Third Step

The third step is a step of removing the protective group of the phenytoin derivative of formula (IV) to form the phenytoin derivative of formula (V).

The removal of the protective group from the compound of formula (IV) can be conducted by a method known per se according to the type of the protective group. The aforesaid protective group can be removed by the treatment with an acid in an inert solvent. Examples of the acid include trifluoroacetic acid, hydrogen chloride, and hydrogen bromide.

The amount of the acid is generally 10 to 100 equivalents based on the phenytoin derivative of formula (VI).

Examples of the solvent that can be used in the reaction are inert solvents, e.g., halogenated hydrocarbons such as methylene chloride, chloroform and carbon tetrachloride.

Generally, the reaction can efficiently be carried out at a temperature of about $-5°$ to about 30° C.

Fourth Step

The fourth step is a step of forming a carboxylic acid derivative by the reaction of the phenytoin derivative of formula (V) and the carboxylic acid compound.

In forming the carboxylic acid derivative of formula (VI) wherein Y is a carbonyl group (—CO—), a saturated aliphatic dicarboxylic acid anhydride represented by the following formula

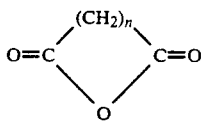

wherein n is as defined above, can be used as the carboxylic acid compound. Examples of the dicarboxylic acid anhydride are succinic anhydride and glutaric anhydride.

The reaction of the compound of formula (V) and the dicarboxylic acid anhydride can be carried out by mixing both of them in the solvent. Examples of the solvent are inert solvents, e.g., amides such as dimethylformamide and dimethylacetamide.

Usually, the reaction can efficiently be conducted at a temperature of about $-5°$ to about 30° C.

It is also possible to form the carboxylic acid derivative of formula (VI) by the reaction of the phenytoin derivative of formula (V) and a dicarboxylic acid or a dicarboxylic acid derivative with one carboxyl group protected by a protective group instead of the dicarboxylic acid anhydride used in this step. It is advisable that the reaction is run in various inert solvents in the presence of a condensation agent. Carbodiimide reagents such as N,N-dicyclohexylcarbodiimide (DCC) and 1-ethyl-3-(3-dimethylaminopropyl)carbodiimide hydrochloride (WSC) are available as the condensation agent.

The protective group of the carboxyl group is an ordinary protective group of a carboxyl group. Examples thereof are a methyl group, an ethyl group, a benzyl group, a p-nitrobenzyl group, a tert-butyl group and a cyclohexyl group. When the reaction is run using the dicarboxylic acid derivative with one carboxyl group protected, the protective group is removed after the reaction, and then can be used in the next step.

The protective group is removed by treatment with an acid. Examples of the acid are hydrogen chloride, anhydrous hydrogen fluoride, methanesulfonic acid, trifluoromethanesulfonic acid, trifluoroacetic acid and a mixture thereof. Reduction with sodium in liquid ammonia or palladium-carbon in an atmosphere of hydrogen is also available.

When forming the carboxylic acid derivative of formula (VI) wherein Y is —CH$_2$—, a halogenated carboxylic acid represented by the formula

wherein Hal denotes a halogen atom such as chlorine, bromine or iodine, and n is as defined above, can be used as the carboxylic acid compound. Examples of the halogenated carboxylic acid include chloroacetic acid, bromoacetic acid, iodoacetic acid, 3-chloropropionic acid, 3-bromopropionic acid, 4-chlorobutyric acid, 4-bromobutyric acid, 5-chlorovaleric acid, 5-bromovaleric acid, 6-chlorohexanoic acid, 6-bromohexanoic acid, 7-chloroheptanoic acid, and 7-bromoheptanoic acid.

It is generally advisable to conduct the reaction of the compound of formula (V) and the halogenated carboxylic acid in the presence of a base. Examples of the base include inorganic bases such as potassium carbonate, sodium carbonate, potassium hydrogencarbonate, sodium hydrogencarbonate, potassium hydroxide and sodium hydroxide; and organic bases such as pyridine and triethylamine. The amount of the base is not strictly limited; it is usually at least 1 equivalent, preferably 1 to 3 equivalents based on the compound of formula (III).

It is advisable to conduct the reaction in a solvent. Examples of the solvent are inert solvents, e.g., amides such as dimethylformamide (DMF); ethers such as diethyl ether, tetrahydrofuran, dioxane and dimethoxyethane; and aromatic hydrocarbons such as benzene, toluene and xylene. They may be used either singly or in combination.

Usually, the reaction can efficiently be carried out at a temperature of about 0° to about 150° C.

It is also possible that the carboxyl group of the halogenated carboxylic acid is protected, as required, by esterification, the above reaction is carried out and then the deprotection reaction is conducted to form the carboxylic acid derivative of formula (VI).

Fifth Step

The fifth step is a step of producing the phenytoin derivative of formula (I) by the condensation reaction of the carboxylic acid derivative of formula (VI) and the uridine derivative of formula (VII).

It is advisable to conduct the condensation reaction in the presence of a condensation agent. Carbodiimide reagents such as N,N-dicyclohexylcarbodimide (DCC), and 1-ethyl-3-(3-dimethylaminopropyl)carbodiimide hydrochloride (WSC) are available as the condensation agent. The amount of the carbodiimide reagent is not strictly restricted; it is usually at least 0.5 mol, preferably 0.5 to 2 mols per mol of the compound of formula (VI).

It is advisable to conduct the reaction in a solvent. Examples of the solvent include halogenated hydrocarbons such as chloroform and dichloromethane; esters such as ethyl acetate; polar organic solvents such as N,N-dimethylformamide and dimethylsulfoxide; ethers such as dioxane and tetrahydrofuran; alcohols such as methanol and ethanol; pyridine; water; and a mixture thereof.

The desirous reaction temperature is usually about $-30°$ C to about $50°$ C.

The phenytoin derivative of formula (I) can also be produced by converting the carboxylic acid derivative of formula (VI) used in this step into an active derivative having various carboxyl groups, and then reacting said derivative with the uridine derivative of formula (VII) in an inert solvent.

Examples of the active derivative with the carboxyl group formed from the compound of formula (VI) are corresponding (mixed) acid anhydride, azide compound and active ester compound. Examples of the active ester compound are esters of alcohols such as pentachlorophenol, 2,4-dinitrophenol, cyanomethyl alcohol, p-nitrophenol, N-hydroxy-5-norbornene-2,3-dicarboxyimide, N-hydroxysuccinic acid imide, N-hydroxyphthalimide and 1-hydroxybenzotriazole.

The uridine derivative of formula (VII) used in this step is a commercially available compound. It is deoxyuridine triphosphate (dUTP) derivative when Z is a hydrogen atom, or an uridine triphosphate (UTP) derivative when Z is a hydroxyl group. M is an alkali metal ion, an alkaline earth metal ion or an ammonium ion. Examples of the alkali metal ion are lithium, sodium and potassium. Examples of the alkaline earth metal are magnesium, calcium and barium.

Examples of the deoxyuridine derivative and the uridine derivative represented by formula (VII) include tetraammonium 5-(3-amino-1-propenyl)-2'-deoxyuridine-5'-triphosphate, tetrasodium 5-(3-amino-1-propenyl)-2'-deoxyuradine-5'-triphosphate, tetrapotassium 5-(3-amino-1-propenyl)-2'-deoxyuridine-5'-triphosphate, tetraammonium 5-(3-amino-1-propenyl)-2'-uridine-5'-triphosphate, tetrasodium 5-(3-amino-1-propenyl)-2'-uridine-5'-triphosphate, and tetrapotassium 5-(3-amino-1-propenyl)-2'-uridine-5'-triphosphate.

The compound produced in the above steps can be separated and purified, after the reaction, by a method known per se, such as extraction, reprecipitation, recrystallization, or various chromatographies, as required.

The phenytoin derivative of formula (I) provided by this invention is useful to form a phenytoin-labelled nucleic acid probe by introducing said derivative into a nucleic acid probe.

The phenytoin-labelled nucleic acid probe can be produced, like the ordinary biotin-labelled nucleic acid probe, from the phenytoin derivative of formula (I) in this invention and various nucleotides and/or DNA or RNA fragments using various polymerases.

For example, the phenytoin-labelled DNA probe can be produced by a nick translation method known per se [see, e.g., J. Mol. Biol., 113, 237 (1977)], a random primed labelling method [see, e.g., Anal. Bio, Chem., 132, 6 (1983)], or a 3'-end labelling method [see, e.g., Methods in Enzymology, 65, 499-560 (1980)], using the phenytoin derivative of formula (I) wherein Z is a hydrogen atom and a DNA polymerase such as *Escherichia coli* DNA polymerase I, DNA polymerase of bacteriophage T4, mouse or human cell-derived DNA polymerase $\alpha$ or $\beta$, or herpes simplex DNA polymerase.

Said probe can also be produced by a reverse transcription method using reverse transcriptases such as Rous related virus 2, avian myeloblastosis virus, etc. [see, e.g., J. Biol. Chem., 253, 2471-2482 (1978)], and a tailing method [see, e.g., Methods in Enzymology, 100, 96-116 (1983) and Gene, 27, 309-313, (1984)] utilizing an enzyme such as bovin thymus-derived terminal transferase [see, e.g. The Enzymes, compiled by Boger P.D., 10, 145-171 (1971)].

Moreover, the phenytoin-labelled RNA probe can be produced by a transcription method [see, e.g., J. Mol. Biol., 166, 477 (1983)]utilizing, for example, the phenytoin derivative of formula (I) wherein Z is a hydroxyl group and RNA polymerases of phages such as phage SP-6, phage T7 and phage T3.

Detection of a target nucleic acid in a specimen using the thus produced phenytoin-labelled nucleic acid probe can be conducted by a method known per se which is described in Proc. Nath. Acad. Sci. USA, 78, 6633-6637 (1981), J. Clin. Chem. and Clin. Biochem., 27, 130-131 (1989), Nucleic Acids Research, 18, 5843-5851 (1990), Nucleic Acids Research, 13, 745-761 (1985) and Analytical Chemistry, 62, 2258-70 (1970).

For example, detection of a specimen, e.g., DNA such as virus DNA in a serum, using the phenytoin-labelled DNA probe can be carried out in accordance with usual enzyme immunoassay comprising single-stranding a DNA chain of virus in the specimen, immobilizing it in a solid phase, hybridizing the above produced phenytoin-labelled DNA probe therewith, conducting the reaction with an enzymatically labelled antiphenytoin antibody, further adding a substrate to the enzyme, and measuring the amount of color development, the amount of fluorescence or the amount of luminescence (see, e.g., "Enzyme Immunoassay", E. Ishikara, Kyoritsu Shuppan, 1987).

The antibody to phenytoin that can be used in the hybridization with the phenytoin-labelled DNA probe may be either an antiserum (polyclonal antibody) obtained by immunizing phenytoin in an animal or an antiphenytoin monoclonal antibody obtained by a cell fusion method of Koehler and Milstein. As the antiphenytoin monoclonal antibody, monochlonal antibody PHT 16-17 is taken which is produced with hybridoma PHT 16-17 disclosed in Japanese Laid-open Patent Application No. 138992/90 and deposited as FERM P-10389 in Microorganism Industry Institute, Agency of Industrial Science and Technology, 1-go, 1-ban, 1-chome, Higashi, Tsukuba-shi, Ibaraki-ken, Japan.

The above anti-phenytoin antibody is not necessarily a complete antibody and may be its decomposed fragments such as Fab, Fab', etc.

These antibodies can be enzymatically labelled by a method known per se, e.g., a method described in "Enzyme Immunoassay", E. Ichikawa, Kyoritsu Shuppan, 1987. Examples of the enzyme that can be used at that time are alkali phosphatase, $\beta$-galactosidase and peroxidase. Substrates to these enzymes can be selected depending on types of the enzymes used. For example, in the color development, 5-bromo-4-chloro-3-indolylphosphate can be used to alkali phosphatase; in the chemical luminescence, disodium 3-(2'-spiroadamantane)-4-methoxy-4-(3''-phosphoryloxy)-phenyl-1,2-dioxetane (hereinafter abbreviated as "AMPPD") can be used to alkali phosphatase. The amount of color development, the amount of fluorescence and the amount of luminescence can be measured by methods using a spectrophotometer, a fluorophotometer, a photocounter, and a luminometer, a method in which a signal is observed with an unaided eye by sensitizing a film, and a method using a densitometer and a chemiluminescence reader (CL reader).

Using the aforesaid phenytoin-labelled nucleic acid probe of this invention, the target nucleic acid in the specimen can be detected with high sensitivity, making it possible to detect quite effectively viruses such as viral hepatitis types A, B and C, viruses such as HTLV-1, HIV-I, HIV-II, various pathogenic bacteria, genes of genetic disease, and so forth.

FIG. 1 is a graph that shows the results of HPLC analysis using an ODS column of phenytoin dUTP produced in this invention.

This invention will be illustrated more specifically by the following Examples and Comparative Examples.

EXAMPLE 1

Synthesis of phenytoin-dUTP (1) Synthesis of 6-tert-butoxycarbonylaminohexanol $$H_2N-(CH_2)_6-OH + BOC-ON \longrightarrow$$

$$\underset{\underset{O}{\parallel}}{t\text{-BuOCNH}}-(CH_2)_6-OH$$

Four grams of 6-amino-1-hexanol (34.1 mmols) was dissolved in 30 ml of chloroform and ice-cooled. Seven grams of 2-(tert-butoxycarbonyloxyimino)-2-phenylacetonitrile (BOC-ON) dissolved in 20 ml of chloroform was added, and the mixture was ice-cooled and reacted for 16 hours. Chloroform was evaporated, and the residue was separated and purified by silica gel column chromatography to obtain 6.59 g of the captioned compound. Yield: 89 %.

(2) Synthesis of 3-(6-tert-butoxycarbonylaminohexyl)phenytoin

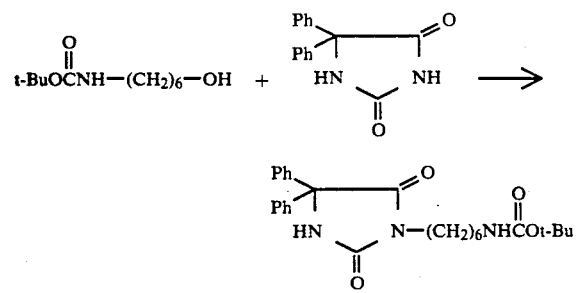

3-(6-Tert-butoxycarbonylamino)hexanol (0.87 g: 4 mmols) was dissolved in 3 ml of pyridine, and ice-cooled, p-Toluenesulfonyl chloride (0.915 g) was added, and the reaction was performed for 2.5 hours. After the reaction, the reaction mixture was charged into 100 ml of ice water, and extracted thrice with ethyl acetate. The organic layer was washed thrice with a 5% sodium hydrogencarbonate aqueous solution and thrice with a 5% citric acid aqueous solution. After drying, the solvent was evaporated. The product was dissolved in 2 ml of dimethylformamide (DMF). Phenytoin (5,5-diphenyl-2,4-imidazolidinedione: 0.504 g) was dissolved in 3 ml of DMF and they were mixed. Calcium carbonate (0.49 g) was added, and the reaction was run at 90° C. for 60 minutes. After the reaction, the reaction mixture was charged in water, and extracted thrice with ethyl acetate. The organic layer was washed once with 5% citric acid and thrice with water, and dried. The product was separated and purified by silica gel column chromatograhy to obtain 0.8 g of the captioned compound. Yield: 44%

¹HNMR [; 1.31 (m, 4H), 1.41 (s, 9H), 1.61 (m, 4H), 3.05 (m, 2H), 3.57 (t, 2H), 4.50 (bs, 1H), 6.24 (bs, 1H), 7.36 (s, 10H)]

(3) Synthesis of 6-(5,5-diphenyl-2,4-imidazolidinedion-3-yl)hexylsuccinamic acid

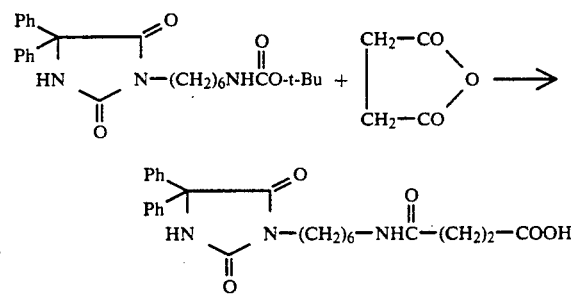

Five-hundred milligrams (1.1 mmols) of 3-(6-tert-butoxycarbonylamidehexyl)phenytoin was dissolved in 1 ml of methylene chloride, followed by adding 1 ml of trifluoroacetic acid. The reaction was run at room temperature for 30 minutes. The solvent was removed by an evaporator, and the reaction product was washed with ether:hexane (1:1) and dried in a vacuum desiccator over sodium hydroxide. The dried product was dissolved in 2 ml of DMF and neutralized with triethylamine (pH 8), followed by adding 170 mg of succinic anhydride. The reaction was performed overnight at room temperature. After the reaction, the reaction mixture was charged in ml of water, adjusted to pH of 3 and extracted thrice with ethyl acetate. The organic layer was washed with a 5% citric acid aqueous solution, water and a NaCl aqueous solution, and then dried. The solvent was evaporated, and the captioned compound was obtained and used in the following step.

(4) Synthesis of N-hydroxysuccinimide 6-(5,5-diphenyl-2,4-imidazolidinedion-3-yl)hexylsuccinamate

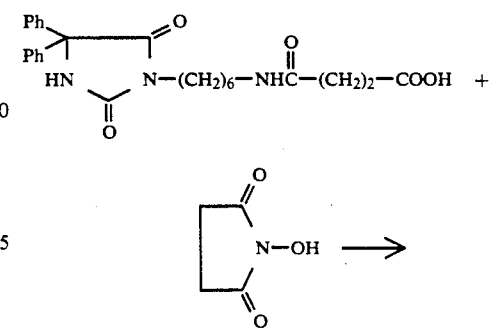

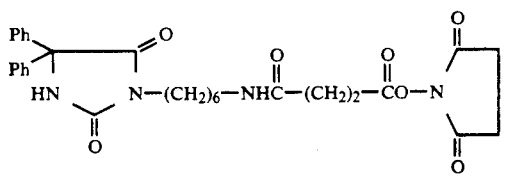

6-(5,5-Diphenyl-2,4-imidazolidinedion-3-yl)hexylsuccinamic acid (0.45 g: 1 mmol) was dissolved in 2 ml of methylene chloride, and ice-cooled, and N-hydroxysuccinimide (1.1 mmols) and N-dicyclohexylcarbodiimide (1.1 mmols: a 50% methylene chloride solution) were added in an amount of 2.2 ml. The reaction was carried out. After the reaction, the precipitate was removed by filtration. After the solvent was removed, the captioned compound was obtained and used in the following step.

(5) Synthesis of phenytoin-dUTP

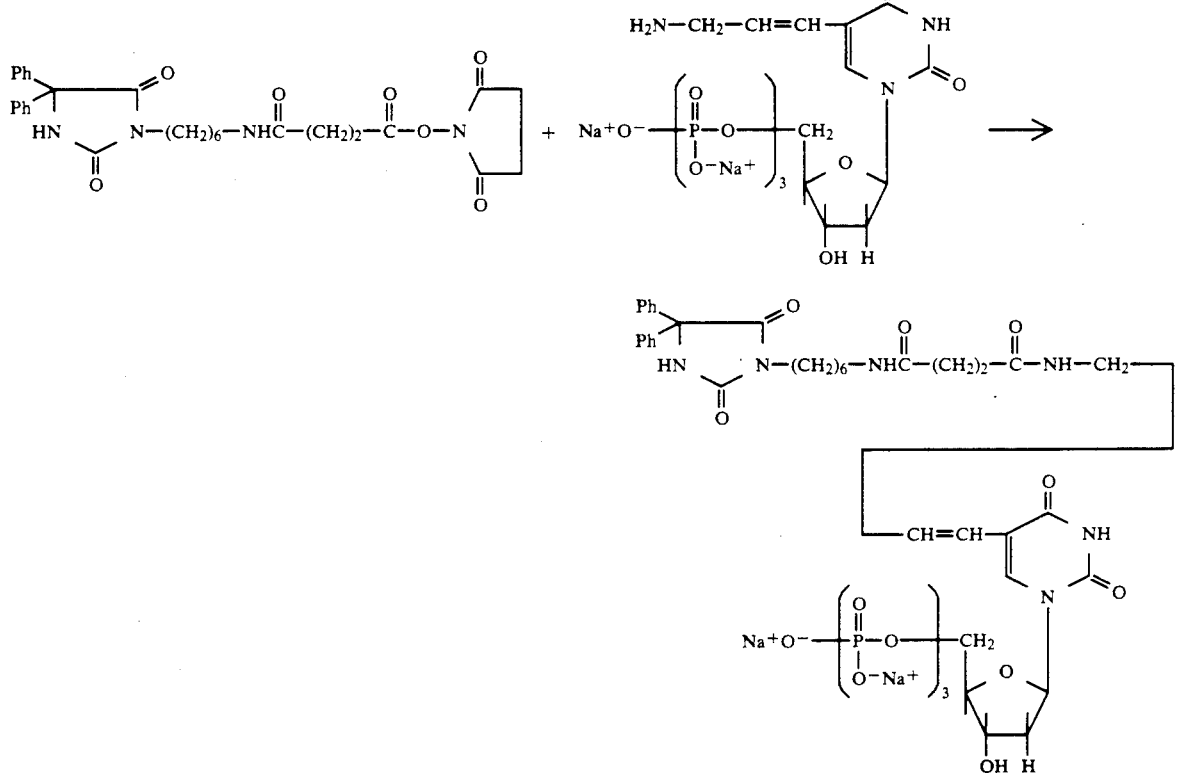

Ten milligrams of tetrasodium deoxyuridine-triphosphate (AAdUTP sodium salt) was dissolved in 3 ml of a borate buffer. Forty milligrams of N-hydroxysuccinimide 6-(5,5-diphenyl-2,4-imidazolidinedion-3-yl)hexylsuccinate was dissolved in 2 ml of DMF. They were reacted at room temperature for 3 hours. The reaction was confirmed with HPLC (gene pack DNA, 25 mM phosphate buffer) through disappearance of AAdUTP. After the reaction, the solvent was evaporated, and purified with triethylamine buffer/50% methanol by DEAE-sephadex A25 column. A fraction of 0.6-0.7M triethylamine buffer/50% methanol was collected to obtain 18 mg of the captioned compound. Yield: 90%

The results of HPLC analysis of the captioned compound are shown in FIG. 1. The measuring conditions are as follows.

| column: | TSK-gel, ODS-120 T (manufactured by Toso K.K.), 4.6 mm ID × 150 mm L |
|---|---|
| eluent: | 50 mM sodium acetate buffer (pH 4.6): acetonitrile = 9:1 to 4:6 straight concentration gradient |
| column temperature: | 55° C. |
| detection wavelength: | 280 nm |

EXAMPLE 2

Labelling of DNA With Phenytoin dUTP by Random Primed Labelling

One microgram of HBV.DNA (adr) split with a restriction enzyme was labelled with DNA polymerase I (klenow fragment) in the presence of 1 $\mu$M of dATP, 1 $\mu$M of dCTP, 1 $\mu$M of dGTP, 0.65 $\mu$M of dTTP and 0.35 $\mu$M of phenytoin dUTP produced in Example 1. After the labelling, labelled DNA was purified by ethanol precipitation.

EXAMPLE 3

Detection of Viral Hepatitis Type B (HBV) DNA

HBV.DNA (adr) cloned in plasmid DNA was purified by ultracentrifugation, treated with a restriction enzyme, separated by agarose gel electrophoresis, and quantitatively determined by measurement with UV$_{260}$. The thus treated HBV.DNA was diluted to an intended concentration, modified with an alkaline solution, dot-blotted on a nylon membrane and neutralized with a neutralizing solution, followed by immobilizing HBV.DNA with UV. After hybridization at 60° C. for 4 hours, the phenytoin-labelled HBV.DNA (Example 2) was hybridized at 60° C. for 16 hours at a concentration of 50 mg/ml. After the hybridization, the hybrid was washed with 2×SSC and 0.1% SDS and then with 0.5×SSC and 0.1% SDS to remove aspecific probes. The alkaline phosphatase-labelled antiphenytoin antibody was reacted and washing was conducted. AMPPD was added, and an X-ray film was sensitized with luminescence. The blotted HBV.DNA was detected with a CL reader (MICROLIGHT ML-1000 manufactured by Dynatech). HBV.DNA in each concentration is shown in Table 1.

TABLE 1

Detection of HBV.DNA

| HBV.DNA (pg) | CL count |
|---|---|
| 100 | 4.563 |
| 50 | 3.200 |
| 25 | 2.335 |
| 12 | 1.933 |
| 6 | 1.689 |
| 3 | 1.516 |
| 1.6 | 1.104 |
| 0.8 | 1.002 |
| 0.4 | 0.927 |
| 0.2 | 0.853 |
| 0.1 | 0.948 |
| 0 | 0.761 |

EXAMPLE 4

Detection of Viral Hepatitis Type B (HBV) DNA From a Serum Sample

Three-hundred microliters each of positive and negative serum specimens was charged in a sample tube and centrifuged (15 Krpm, 10 minutes, 4° C.) to remove a dust in the serum. Fifty microliters of the serum in the intermediate layer was charged into a separate sample tube, and an alkaline modification solution (0.5N-NaOH, 1M-NaCl, 0.3% NP 40) was added. The solution was left to stand at room temperature for 10 minutes. The resulting substance was dot-blotted on a nylon membrane previously attached to 2xSSC, neutralized with a neutralizing solution and immobilized with UV. Plasmid DNA (cloned HBV.DNA adr) purified by ultracentrifugation was used as standard DNA. After prehybridization at 60° C. for 4 hours, the phenytoin-labelled HBV.DNA (Example 2) was hybridized in a concentration of 50 mg/ml at 60° C. for 16 hours. After the hybridization, washing was conducted with 2xSSC and 0.1% SDS, and at 60° C. with 0.5 xSSC and 0.1% SDS to remove aspecific probes. The alkaline phosphatase-labelled antiphenytoin antibody was reacted and washing was conducted. Then, AMPPD was added and an X-ray film was sensitized with luminecence. The blotted HBV.DNA was detected with the same CL reader as used in Example 3. The results of measuring the positive and negative serums are shown in Tables 2 and 3.

TABLE 2

Detection of HBV.DNA in a positive serum

| | CL count |
|---|---|
| positive serum 1 | 1.942 |
| 2 | 5.246 |
| 3 | 1.718 |
| 4 | 3.396 |

TABLE 3

Detection of HBV.DNA in a negative serum

| | CL count |
|---|---|
| negative serum 1 | 0.636 |
| 2 | 0.546 |
| 3 | 0.536 |
| 4 | 0.664 |

What we claim is:

1. A phenytoin derivative represented by formula (I)

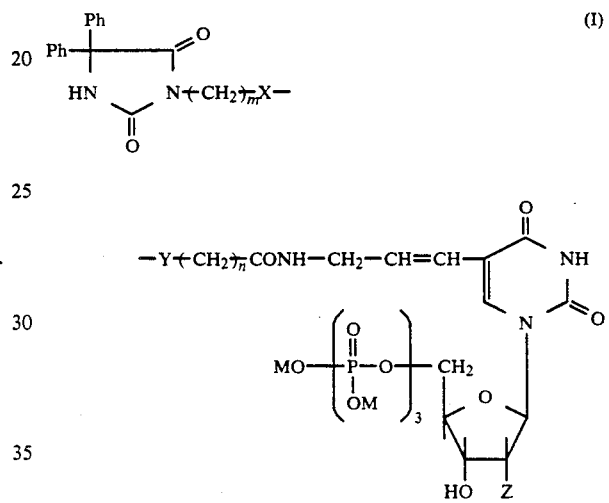

wherein

Ph denotes a phenyl group,

X denotes —O—, —NH— or —CH$_2$—,

Y denotes —CO— or —CH$_2$—,

Z denotes a hydrogen atom or a hydroxyl group,

M denotes a salt-forming cation, and m and n are each an integer of 0 to 8 and m+n is from 2 to 16.

2. The phenytoin derivative of claim 1 wherein m is an integer of 4 to 6.

3. The phenytoin derivative of claim 1 wherein n is an integer of 2 to 3.

4. The phenytoin derivative of claim 1 wherein m+n is 6 to 9.

5. The phenytoin derivative of claim 1 wherein the salt-forming cation is an alkali metal ion, an alkaline earth metal ion or an ammonium ion.

6. The phenytoin derivative of claim 1 wherein m is an integer of 4 to 6, n is an integer of 2 to 3 and m+n is 6 to 9.

7. A phenytoin derivative according to claim 1 having the formula

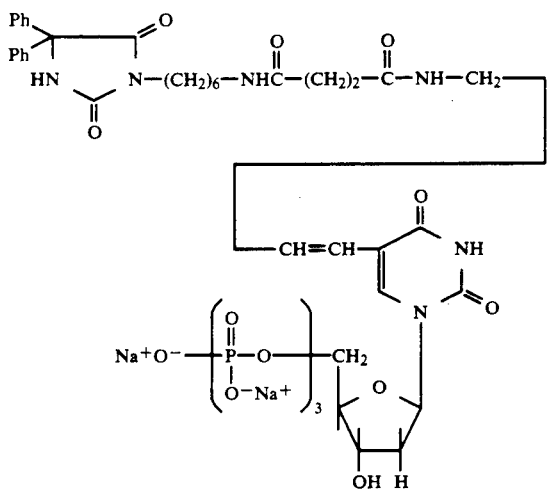

8. A phenytoin-labelled nucleic acid probe having introduced therein the phenytoin derivative of formula (I) as recited in claim 1.

9. The phenytoin-labelled nucleic acid probe of claim 8 which is a phenytoin-labelled DNA probe.

10. A method of detecting DNA in a specimen suspecting of containing same which comprises single-stranding the target DNA in the specimen, immobilizing the single-stranded DNA chain in a solid phase, hybridizing therewith the phenytoin-labelled DNA probe as recited in claim 7, reacting the hybridized produce with an enzymatically labelled anti-phenytoin antibody, further adding a substrate to the enzyme, and measuring the amount of color development, fluorescence or luminescence as a measure of the presence of the target DNA in the specimen.

11. The method of claim 10 wherein the target DNA is a viral DNA.

12. The method of claim 10 wherein the target DNA is viral hepatitis-type B DNA.

* * * * *